United States Patent [19]

Vallejos et al.

[11] Patent Number: 5,616,733
[45] Date of Patent: Apr. 1, 1997

[54] PREPARATION METHOD FOR 2-COUMARANONE

[75] Inventors: Jean-Claude Vallejos, Paris; Alain Perrard, Sainte Foy les Lyon; Yani Christidis, Paris; Pierre Gallezot, Lyons, all of France

[73] Assignee: Societe Francaise Hoechst, Puteaux, France

[21] Appl. No.: 472,400

[22] Filed: Jun. 7, 1995

[30] Foreign Application Priority Data

Jun. 22, 1994 [FR] France .................................. 94 07651

[51] Int. Cl.⁶ .................................................. C07D 307/78
[52] U.S. Cl. .............................................................. 549/307
[58] Field of Search ............................................. 549/307

[56] References Cited

FOREIGN PATENT DOCUMENTS 0041656 12/1981 European Pat. Off. .
2686880 6/1993 France .

OTHER PUBLICATIONS

Mondon et al, Neue Abkommlinge der Cyclohexanon–(1)–essigsaure–(2)' Chemische Berichte, vol. 96, pp. 826–839, 1963.

T. Fukagawa et al, Palladium–Promoted Intramolecular Aromatic Actloxylation: Preparation of 2–Coumaranone, The Journal of Organic Chemistry, vol. 47, No. 12, pp. 2491–2493, Jun. 4, 1982.

*Primary Examiner*—Amelia Owens
*Attorney, Agent, or Firm*—Browdy and Neimark

[57] ABSTRACT

Preparation process for 2-coumaranone in which glyoxylic acid, in vapor phase, is reacted with cyclohexanone, in the presence of a dehydrogenation catalyst.

21 Claims, No Drawings

PREPARATION METHOD FOR 2-COUMARANONE

A subject of the present invention is a preparation process for 2-coumaranone, also called 3H-2-benzofuranone.

2-coumaranone is a known product, widely described in the literature (cf. Beil. 17, 309; I, 159; II, 331). It is the lactone of orthohydroxyphenylacetic acid and it is used as a basic material in organic synthesis to obtain various products intended for agricuture or having physiological effects. Therefore, processes are continually being sought which allow it to be obtained rapidly and cheaply from inexpensive commercially-available products. Now, the Applicant was surprised to discover a rapid preparation process for 2-coumaranone from glyoxylic acid and cyclohexanone.

Therefore a subject of the present invention is a preparation process for 2-coumaranone characterized in that glyoxylic acid, in vapour phase, is reacted with cyclohexanone, in the presence of a dehydrogenation catalyst.

By the expression "dehydrogenation catalyst" is meant a catalyst known for the aromatization of rings with 6 members such as those mentioned in Advanced Organic Chemistry, Jerry March, 3rd edition, pages 1052–1054, J. Willey, Interscience, New York, 1985, as well as in Houben-Weyl, Phenole, Tome 2, pages 701–716, Georg Thieme-Stuttgart, 1976. Preferably the dehydrogenation catalyst is chosen from the group constituted by palladium and platinum.

Under preferred conditions for implementing the invention, the process described above is carried out in the following manner:

at a temperature greater than or equal to 150° C., using a supporting gas constituted by a mixture of 0 to 100% dinitrogen, N2, and 100 to 0% dihydrogen, H2, by dissolving glyoxylic acid and cyclohexanone in a solvent or a mixture of solvents having a boiling point of less than 150° C., preferably in acetic acid or a water-acetic acid mixture, using approximately stoichiometrical quantities of glyoxylic acid and cyclohexanone, or a slight excess of cyclohexanone, using a platinum- or palladium-based catalyst placed on an inert solid support such as $\alpha$ alumina, $\gamma$ alumina, silica, silicon carbide, charcoal, having a specific surface area greater than 1 $m^2$ per gram and preferably greater than 50 $m^2$ per gram, at a concentration greater than or equal to 0.5% by weight.

Under more preferable conditions, the process described above is implemented by passing a gaseous mixture resulting from the evaporation of a solution in acetic acid containing equi-molecular quantities of cyclohexanone and glyoxylic acid in aqueous solution in a supporting gas constituted by dinitrogen and dihydrogen in variable proportions over a catalytic bed constituted by metallic palladium deposited on charcoal, at a temperature greater than 200° C.

According to a variant of the invention, the process described above is carried out in two stages: in a first stage, glyoxylic acid is reacted according to a known process with cyclohexanone in order to obtain a mixture in variable proportions of (2-oxo cyclohexylidene) acetic acid in its different stereoisomeric forms and/or in the form of various internal y lactones, then, in a second stage, 2-coumaranone is prepared by passing the crude reaction mixture obtained in the first stage, in the form of a vapour, over a dehydrogenation catalyst identical to that used previously.

Therefore a subject of the invention is also a preparation process for 2-coumaranone characterized in that the crude reaction product obtained by condensation, carried out according to a process known per se, of glyoxylic acid with cyclohexanone is passed, in the form of a vapour, over a dehydrogenation catalyst, identical to that defined previously.

Under preferred conditions for implementing the variant of the invention, the process described above is carried out in the following manner:

the condensation of glyoxylic acid with cyclohexanone is carried out at a temperature greater than 50° C., in solution in a mixture constituted by 0 to 100% of water and 100 to 0% of acetic acid, with stoichiometric quantities of reagents and a concentration comprised between 10 and 50% by weight, the crude reaction mixture of the condensation of glyoxylic acid with cyclohexanone is vaporized at a temperature greater than or equal to 150° C., then it is entrained over the catalyst using a supporting gas constituted by a mixture of 100 to 0% of dinitrogen and 0 to 100% of dihydrogen, the catalyst is based on platinum or palladium deposited on an inert solid support such as $\alpha$ alumina, $\gamma$ alumina, silica, silicon carbide, charcoal, having a specific surface area greater than 1 $m^2$ per gram and preferably greater than 50 $m^2$ per gram, at a concentration greater than or equal to 0.5%.

2-coumaranone is isolated from the gaseous mixture by means known per se. Preferably, the gaseous mixture is cooled down to ambient temperature, then the 2-coumaranone formed is isolated by distillation, the non-converted starting products are recycled and so is/are the solvent or solvents.

During the dehydrogenation reaction of (2-oxo cyclohexylidene) acetic acid into 2-coumaranone, under certain operating conditions, the formation of 2-cyclohexanone acetic acid and 2-cyclohexanol acetic acid as by-products of the reaction, in significant quantities, is observed.

These products can also be prepared by other synthesis routes: Melvin S. N. et al J. Am. Chem. Soc., p 233, February 1945; Mondon A. et al, Chem. Ber., 96, 826 (1963).

2-cyclohexanone acetic acid and 2-cyclohexanol acetic acid also lead to the formation of 2-coumaranone if they are subjected to the dehydrogenation process described above.

Therefore a subject of the invention is also a preparation process for 2-coumaranone characterized in that 2-cyclohexanone acetic acid or 2-cyclohexanol acetic acid, in vapour phase, are passed over a dehydrogenation catalyst.

This property is particularly useful since it allows the by-products of the conversion reaction of (2-oxo cyclohexylidene) acetic acid into 2-coumaranone to be collected, in order to recycle them as starting products in the same process.

The condensation of glyoxylic acid with cyclohexanone in order to obtain (2-oxo cyclohexylidene) acetic acid in its different stereoisomeric and/or lactonic forms as well as the different products obtained are described in particular in DE-A-1, 995,375 and by K. W. Rosenmund et al, Arch. Pharm., 287, 441, (1954); A. Mondon et al, Chem. Ber., 96, 826, (1963); A. W. Noltes et al, Rec. Trav. Chim., 80, 1334 (1961); Y. Arbuzov et al, Zhur. Obschei Khim., 32, 3676 (1962); M. N. KOLOSOV et al, Zhur. Obschei Khim., 32, 2983, (1962); F. BONADIES et al, Gazz. Chim., Ital., 113, 421 (1983).

The following examples illustrate the invention without however limiting it.

EXAMPLE 1

A solution containing:

736 g (7.5 moles) of cyclohexanone, 694 g of glyoxylic acid at 80% by weight in water, that being 7.5 moles of 100% glyoxylic acid, 3520 g of pure acetic acid, is heated under reflux for 24 hours then the solution obtained is concentrated under reduced pressure until a weight of 3520 g is obtained. At this stage, this solution, designated S1, contains:

3.2% of unconverted cyclohexanone,

9% of (2-oxo cyclohexylidene) acetic acid, trans isomer, designated 1, described by M. N. Kolosov et al, 17% of the lactone of (2,2-dihydroxy cyclohexylidene) acetic acid, designated 2, described in particular by Yu Wang et al, Hua Hsueh Hsueh Pao, 26 (2), 84 (1960), and 28 (6) 351 (1962), 1.3% of the lactone of (2-hydroxy 2-cyclohexene ylidene) acetic acid, designated 3, described by Yu Wang et al, 69.5% of acetic acid.

These analyses were carried out by high performance liquid chromatography and by acidimetry.

EXAMPLE 2

A solution containing:

245 g (2.5 moles) of cyclohexanone, 296 g of a commercial aqueous solution of glyoxylic acid at 50% by weight, that being 2 moles of glyoxylic acid, 228 g of pure acetic acid, is heated for 90 minutes at 130° C., under pressure in a closed reactor, then the reaction medium is cooled down to ambient temperature. In this way a solution, designated S2, is obtained, containing by weight:

9% of cyclohexanone,

15% of 1,

19% of 2,

57% of an acetic acid-water mixture.

EXAMPLES 3–9

Solution S1 is vaporized in a vaporizer maintained at a temperature of 200° C. with a flow rate of 6 ml/hr and the vapours are entrained in a dinitrogen current with a flow rate of 200 Nl/hr (1 Nl=22.4 l) towards the reactor maintained at a temperature of 250° C.

The reactor is a vertical cylinder with an inner diameter of 26 mm and a length of 200 mm, sealed at its lower end with sintered glass, with a useable volume of 80 ml, filled with 2mm diameter glass beads, in the following manner: 15 ml of glass beads, then M g of a catalyst Ca diluted with 20 ml of glass beads and finally 40 ml of glass beads. The mass M of catalyst Ca corresponds to a constant mass of active metal of 0.05 g. At the outlet of the reactor, the hot gases are cooled down and condensed by passing them into traps immersed in liquid nitrogen. The products condensed in the traps are collected then analyzed by high performance liquid chromatography (HPLC). The results obtained after two hours of operation, as a function of the catalyst, are given in table A in which OCR means "overall conversion rate" and SC the "selectivity of the reaction" for 2-coumaranone.

$$OCR = \frac{\Sigma m(\text{products formed})}{\Sigma m(\text{residual reagents}) + \Sigma m(\text{products formed})}$$

$$SC = \frac{m(\text{2-coumaranone})}{\Sigma m(\text{products formed})}$$

$\Sigma m$ designates the sum of the masses designates the mass of a product

EXAMPLE 10

The operation is carried out as in Examples 3 to 9 using S2 as the starting product, which is injected at a flow rate of 12 ml/hr, with a total quantity of 250 mg of palladium deposited at 2.5% on α alumina as catalyst (catalyst G). The products of the reaction are trapped in acetonitrile for one hour.

TABLE A

| Catalyst Ca | OCR (%) | SC (%) |
|---|---|---|
| A - 2.5% Pd/C, prepared in the laboratory | 97 | 91 |
| B - 1% Pd/C, from DEGUSSA E 152 × H/D | 83 | 88 |
| B - 1% Pd/C, from DEGUSSA E 152 × ground H/D | 98 | 87 |
| C - 0.8% Pd/C, from JOHNSON MATTHEY type 86 | 78 | 91 |
| D - 0.8% Pd/C, from ENGELHARD ES Cat 19 | 91 | 89 |
| E - 0.5% Pd/C, from ENGELHARD Code 4586 | 23 | 65 |
| F - 0.5 Pt/Al2O3, γ alumina, from ENGELHARD Code 4751 | 29 | 83 |
| G - 2.5% Pd/Al2O3, α alumina prepared in the laboratory | 70 | 80 |

Catalyst A prepared in the laboratory was obtained in the following manner:

100 g of NORIT ROX 0.8 charcoal in the form of granules (1=3 mm, diameter 0.8 mm) is treated at about 0° C. with 825 ml of an aqueous solution of sodium hypochlorite titrated at 4.8% of active chlorine, then the solid is successively washed with 1.25N hydrochloric acid and water before being dried under reduced pressure at 100° C. 38 g of oxidized charcoal obtained previously is introduced into 600 ml of 1N ammonium hydroxide, then 5 g of palladium tetraamine chloride dissolved in 40 ml of water is introduced under agitation into this suspension. After agitation for 16 hours, the solid is isolated, washed with water, dried at 100° C. under an inert atmosphere, then it is progressively heated to 200° C. under a current of argon and finally it is treated with a current of dihydrogen (250 ml/min) from 20° to 300° C. (1° C./min) then for 3 hours at 300° C before being cooled down to 20° C. under dihydrogen. Finally, it is treated with a current of dinitrogen (50 ml/min) containing 1% of dioxygen for 2 hours. In this way a catalyst is obtained containing 2.5% by weight of palladium.

Catalyst G prepared in the laboratory was obtained in the following manner:

In a beaker, 9.527 g of α alumina, with a specific surface area of 10 m$^2$/g, marketed by the Degussa Company under the support material name No. 272, is impregnated with an acid solution of sodium tetrachloropalladate, that being 0.7013 g of sodium tetrachloropalladate dissolved in 1 ml of 36% hydrochloric acid, to which the necessary quantity of water to recover the alumina grains is added.

The mixture is dried in the open air at a temperature of 50° C. for 16 hours, then under reduced pressure at 100° C. for eight hours.

The catalyst obtained is reduced with a diffused current of dihydrogen at a flow rate of 15 l/hr whilst the temperature is raised from ambient temperature to 200° C. at the rate of 1° C./min.

The catalyst is allowed to return to ambient temperature under a current of dihydrogen then it is put under argon.

EXAMPLES 11–12

In the same apparatus as that used in Examples 3–9, the operation is carried out starting with solution S2 and using 5 g of catalyst B with 1% of palladium deposited on charcoal marketed by the DEGUSSA Company under the reference E 152 X H/D. The vaporizer is maintained at a temperature of 200° C., the flow rate of solution S2 is 6 ml/hr and the flow rate of the supporting gas is 200 Nl/hr. The other operating conditions as well as the results obtained are set out in Table B.

TABLE B

| EXAMPLES | 11 | 12 |
| --- | --- | --- |
| Supporting gas: | | |
| nature | $H_2/N_2$ | $H_2$ |
| compositions % | 6/94 | 100 |
| Duration of the operation (hr) | 6 | 8 |
| OCR (%) | 89 | 98 |
| SC (%) | 82.5 | 58 |

EXAMPLE 13

245 g (2.5 moles) of cyclohexanone and 296 g of a commercial aqueous solution of glyoxylic acid at 50% by weight, that being 2 moles, are dissolved in 228 g of pure acetic acid. In this way a solution designated S3 is obtained.

In the same apparatus as that used in Examples 3–12, the reaction is carried out starting with solution S3, using 5 g of catalyst B with 1% of palladium deposited on charcoal marketed by the DEGUSSA Company under the reference E 152 X H/D.

The vaporizer is maintained at a temperature of 200° C. The reactor is maintained at a temperature of 300° C., the supporting gas is a mixture of dinitrogen and dihydrogen 96/4, and its flow rate is 300 Nl/hr. The flow rate of solution S3 is 6 ml/hr.

After operating for two hours, an OCR of 14% and an SC of 20% are obtained.

EXAMPLE 14

Determination of 2-cyclohexanone acetic acid.

Solution S2 is introduced into the tubular 0 reactor of Examples 3 to 13, containing 0.05 g of catalyst B, at a flow rate of 6 ml/hr and under a flow rate of dihydrogen of 200 Nl/hr, the temperature of the vaporizer being 220° C. and that of the reactor 250° C.

After operating for 20 hours, the aerosol is trapped in acetonitrile for one hour, at the outlet of the reactor.

The yield in moles of each of the supply products is measured by HPLC and GC analysis.

| PRODUCT | YIELD |
| --- | --- |
| 2-coumaranone | 29.8% |
| orthocresol | 2.3% |
| phenylacetic acid | 1.9% |
| 2-cyclohexanone acetic acid | 14.9% |
| lactone of 2-cyclohexanol acetic acid | 1.3% |

EXAMPLE 15

Dehydrogenation of the 2-cyclohexanone acetic acid.

A solution at 40% by weight of 2-cyclohexanone acetic acid in acetic acid is prepared.

The preceding acetic solution is introduced into a tubular reactor containing 70 mg of metal Pd deposited at 0.5% on alumina (Engelhardt type catalyst Escat 16) at a flow rate of 10 ml/hr and under a current of nitrogen of 200 Nl/hr.

The temperature of the vaporizer is 220° C. and that of the reactor is 250° C.

After trapping during one hour of operation by bubbling into 150 ml of acetonitrile cooled down using an ice-water bath, the yields in moles of the products formed are measured by HPLC and GC.

| PRODUCT | YIELD |
| --- | --- |
| 2-coumaranone | 19.1% |
| orthocresol | 9.6% |
| phenylacetic acid | 2.3% |
| lactone of cyclohexanolacetic acid | 6% |
| toluene | 4.4% |

We claim:

1. A process for preparing 2-coumaranone, comprising:
   (1) reacting glyoxylic acid with cyclohexanone using an amount of cyclohexanone from approximately stoichimetric to a slight excess relative to said glyoxylic acid, in a solvent having a boiling point of less than 150° C.; and
   (2) dehydrogenating the resultant reaction products over a dehydrogenation catalyst deposited on an inert solid support in vapor phase using a supporting gas.

2. A process for preparing 2-coumaranone, comprising passing a crude reaction product obtained by condensation of glyoxylic acid with cyclohexanone, in the vapor state, over a dehydrogenation catalyst on an inert solid support and using a supporting gas.

3. A process for preparing 2-coumaranone, comprising passing a solution of at least one of 2-cyclohexanone acetic acid and 2-cyclohexanol acetic acid over a dehydrogenation catalyst deposited on an inert support in vapor phase using a supporting gas.

4. A process according to claim 1 further comprising after said dehydrogenation, recycling by-products of the reaction including 2-cyclohexanol acetic acid and 2-cyclohexanone acetic acid.

5. Process according to claim 1, characterized in that said supporting gas is constituted by a mixture of 100 to 0% of dinitrogen and 0 to 100% of dihydrogen in order to entrain the reaction mixture over the dehydrogenation catalyst.

6. Process according to claim 1, characterized in that the operation is carried out at a temperature higher than or equal to 150° C.

7. Process according to claim 1, characterized in that the dehydrogenation catalyst is palladium or platinum.

8. Process according to claim 1, characterized in that said inert solid support having a specific surface area greater than 1 m² per gram.

9. Process according to claim 1, characterized in that said inert solid support having a specific surface area greater than 50 m² per gram.

10. A process according to claim 1, wherein said solvent is acetic acid or a mixture of water and acetic acid.

11. A process according to claim 2 further comprising after said dehydrogenation, recycling by-products of the reaction including 2-cyclohexanol acetic acid and 2-cyclohexanone acetic acid.

12. Process according to claim 2, wherein supporting gas is selected from the group consisting of dinitrogen, dihydrogen and mixtures thereof.

13. Process according to claim 12, carried out at a temperature higher than or equal to 150° C.

14. Process according to claim 13, wherein the dehydrogenation catalyst is palladium or platinum.

15. Process according to claim 14, wherein inert solid support has a specific surface area greater than 1 m² per gram.

16. Process according to claim 15, wherein said inert solid support has a specific surface area greater than 50 m² per gram.

17. Process according to claim 16, wherein said glyoxylic acid and cyclohexanone are dissolved in acetic acid or in a water-acetic acid mixture.

18. Process according to claim 3, further comprising recycling of by-products of the reaction, 2-cyclohexanol acetic acid and 2-cyclohexanone acetic acid.

19. Process according to claim 18, wherein said supporting gas being selected from the group consisting of dinitrogen, dihydrogen and mixtures thereof.

20. Process according to claim 19, carried out at a temperature of at least 150° C. and wherein said dehydrogenation catalyst is palladium or platinum and said inert solid has a specific surface area greater than 1 m²/g.

21. A process according to claim 20, wherein said inert solid support has a specific surface area greater than 50 m²/g.

* * * * *